United States Patent
Lundberg et al.

[11] Patent Number: 6,013,281
[45] Date of Patent: *Jan. 11, 2000

[54] METHOD OF MAKING A PHARMACEUTICAL DOSAGE FORM COMPRISING A PROTON PUMP INHIBITOR

[75] Inventors: Per Johan Lundberg, Mölndal; Kurt Lövgren, Mölnlycke, both of Sweden

[73] Assignee: Astra Aktiebolag, Sodertalje, Sweden

[*] Notice: This patent is subject to a terminal disclaimer.

[21] Appl. No.: 08/612,951

[22] PCT Filed: Feb. 9, 1996

[86] PCT No.: PCT/SE96/00161

§ 371 Date: Mar. 8, 1996

§ 102(e) Date: Mar. 8, 1996

[87] PCT Pub. No.: WO96/24338

PCT Pub. Date: Aug. 15, 1996

[30] Foreign Application Priority Data

Feb. 9, 1995 [SE] Sweden .................................. 9500478

[51] Int. Cl.⁷ .................................. A61K 9/22; A61K 9/30
[52] U.S. Cl. .................... 424/468; 424/467; 424/465; 424/490; 424/475; 424/469; 514/925
[58] Field of Search ..................... 424/468, 467, 424/465, 490, 475, 469; 514/925

[56] References Cited

U.S. PATENT DOCUMENTS

| | | |
|---|---|---|
| 4,628,098 | 12/1986 | Nohara et al. . |
| 4,758,579 | 7/1988 | Kohl et al. . |
| 4,786,505 | 11/1988 | Lovgren et al. . |
| 4,786,650 | 11/1988 | Lovgren et al. .......... 424/468 |
| 4,853,230 | 8/1989 | Lovgren et al. . |
| 5,026,560 | 6/1991 | Makino et al. .......... 424/494 |
| 5,045,321 | 9/1991 | Makino et al. .......... 424/475 |
| 5,093,132 | 3/1992 | Makino et al. .......... 424/475 |
| 5,232,706 | 8/1993 | Palomo Coll .......... 424/475 |
| 5,626,875 | 5/1997 | Ballester Rodes .......... 424/464 |
| 5,690,960 | 11/1997 | Bengtsson et al. .......... 424/480 |
| 5,753,265 | 5/1998 | Bergstrand et al. .......... 424/474 |
| 5,817,338 | 10/1998 | Bergstrand et al. . |

FOREIGN PATENT DOCUMENTS

| | | |
|---|---|---|
| 0005129 | 10/1979 | European Pat. Off. . |
| 0166287 | 1/1986 | European Pat. Off. . |
| 0174726 | 3/1986 | European Pat. Off. . |
| 0247983 | 4/1987 | European Pat. Off. . |
| 0277741 | 8/1988 | European Pat. Off. . |
| 0365947 | 10/1989 | European Pat. Off. . |
| 0342522 | 11/1989 | European Pat. Off. . |
| 2163747 | 3/1986 | United Kingdom . |
| 9006925 | 6/1990 | WIPO . |
| 9119711 | 12/1991 | WIPO . |
| 9119712 | 12/1991 | WIPO . |
| 9427988 | 12/1994 | WIPO . |
| 9501977 | 1/1995 | WIPO . |
| 9601622 | 1/1996 | WIPO . |
| 9624338 | 2/1996 | WIPO . |

OTHER PUBLICATIONS

Sih et al., Studies on (H+ K+)—ATPase Inhibitors of Gastric Secretion, J. Med. Chem. 34(3) pp. 1049–1062, 1991.

Primary Examiner—Thurman K. Page
Assistant Examiner—Brian K. Seidleck
Attorney, Agent, or Firm—White & Case LLP

[57] ABSTRACT

A new oral pharmaceutical dosage form comprising a core material that contains a proton pump inhibitor, one or more alkaline reacting compounds and optionally pharmaceutical excipients having a water soluble separating layer and an enteric coating layer. The core material as such is alkaline reacting and the separating layer between the alkaline reacting core material and the enteric coating layer is formed in situ as a water soluble salt between the alkaline reacting compound(s) and the enteric coating polymer. The invention also describes a new efficient process for the manufacture of such a dosage form comprising two functionally different layers in one manufacturing step, and its use in medicine.

21 Claims, 2 Drawing Sheets

METHOD OF MAKING A PHARMACEUTICAL DOSAGE FORM COMPRISING A PROTON PUMP INHIBITOR

This application is a 371 of PCT/SE96/00161, filed Feb. 9, 1996.

FIELD OF THE INVENTION

The present invention refers to new pharmaceutical formulations comprising acid labile heterocyclic compounds with gastric inhibitory effect, in the following referred to as proton pump inhibitors. The new formulations are intended for oral use. Furthermore, the present invention refers to a new method for the manufacture of such a formulation and, the use of the new formulations in medicine.

BACKGROUND OF THE INVENTION

The proton pump inhibitors are for example compounds of the general formula I

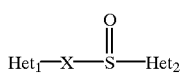
I wherein

Het$_1$ is

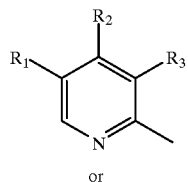

or

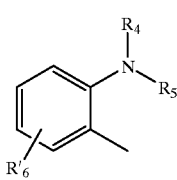

Het$_2$ is

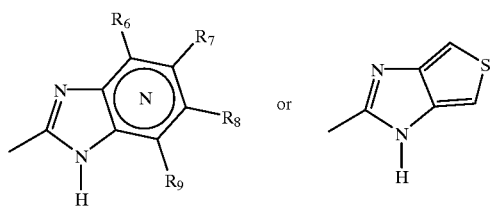

or

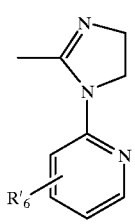

X=

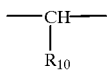 or 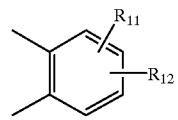

wherein

N in the benzimidazole moiety means that one of the carbon atoms substituted by R$_6$–R$_9$ optionally may be exchanged for a nitrogen atom without any substituents;

R$_1$, R$_2$ and R$_3$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy, R$_4$ and R$_5$ are the same or different and selected from hydrogen, alkyl and aralkyl;

R'$_6$ is hydrogen, halogen, trifluoromethyl, alkyl and alkoxy,

R$_6$–R$_9$ are the same or different and selected from hydrogen, alkyl alkoxy, halogen, halo-alkoxy, alkylcarbonyl, alkoxycarbonyl, oxazolyl trifluoroalkyl, or adjacent groups R$_6$–R$_9$ form ring structures which may be further substituted;

R$_{10}$ is hydrogen or forms an alkylene chain together with R$_3$ and

R$_{11}$ and R$_{12}$ are the same or different and selected from hydrogen, halogen or alkyl or, alkoxy groups. In the above definitions, alkyl groups, alkoxy groups, and moieties thereof may be branched and straight C$_1$–C$_9$-chains or comprise cyclic alkyl groups, for example cycloalkylalkyl.

Examples of proton pump inhibitors according to formula I are

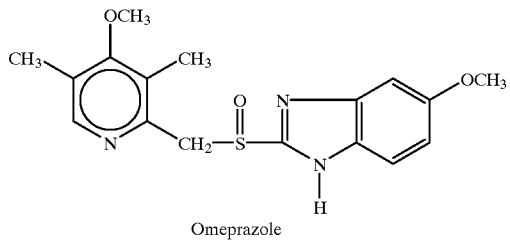
Omeprazole

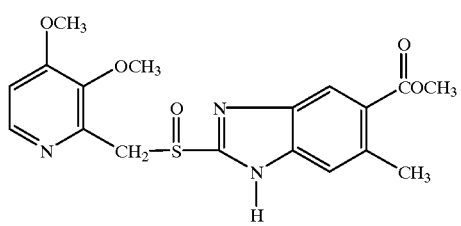

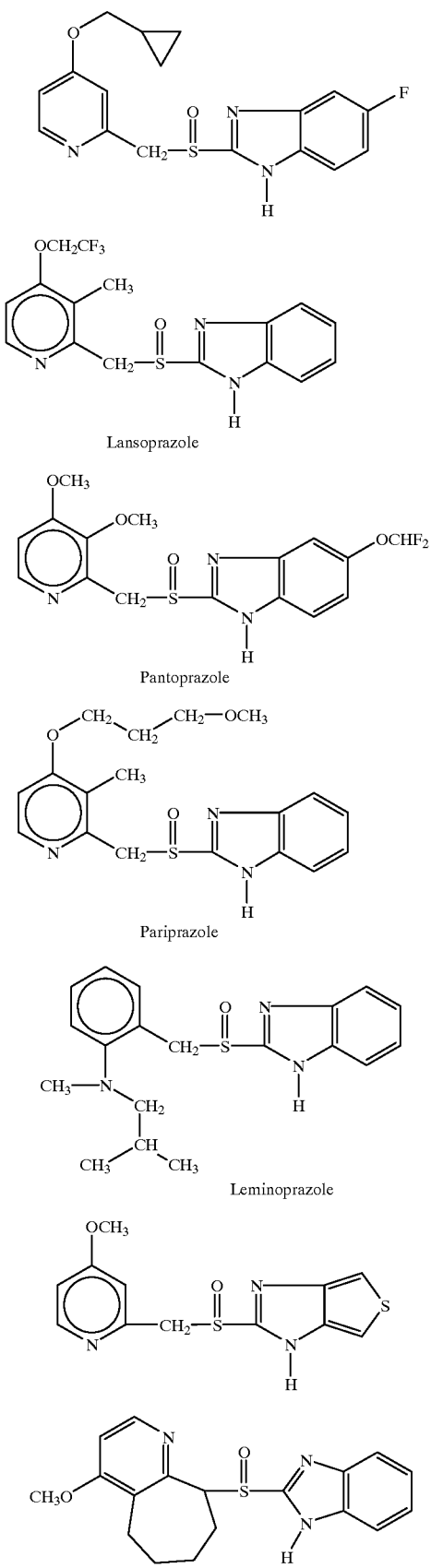

Lansoprazole

Pantoprazole

Pariprazole

Leminoprazole

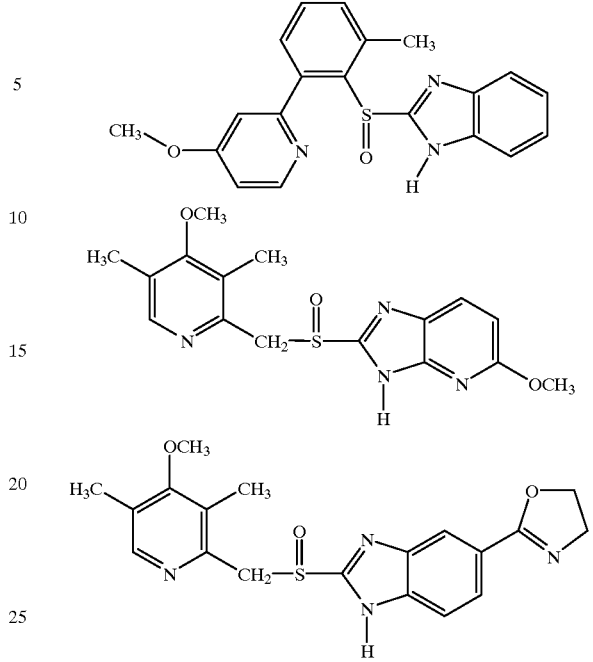

The proton pump inhibitors used in the dosage forms of the invention may be used in neutral form or in the form of an alkaline salt, such as for instance the $Mg^{2+}$, $Ca^{2+}$, $Na^+$, $K^+$ or $Li^+$ salts, preferably the $Mg^{2+}$ salts. Further where applicable, the compounds listed above may be used in racemic form or in the form of a substantially pure enantiomer thereof, or alkaline salts of the racemates or the single enantiomers.

Suitable proton pump inhibitors are for example disclosed in EP-A1-0005129, EP-A1-174 726, EP-A1-166 287, GB 2 163 747 and WO90/06925, WO91/19711, WO91/19712, and further especially suitable compounds are described in WO94/27988 and WO95/01977.

These proton pump inhibitors are, as already mentioned, useful for inhibiting gastric acid secretion in mammals and man. In a more general sense, they may be used for prevention and treatment of gastric-acid related diseases in mammals and man, including e.g. reflux esophagitis, gastritis, duodenitis, gastric ulcer and duodenal ulcer. Furthermore, they may be used for treatment of other gastrointestinal disorders where gastric acid inhibitory effect is desirable e.g. in patients on NSAID therapy, in patients with Non Ulcer Dyspepsia, in patients with symptomatic gastro-esophageal reflux disease, and in patients with gastrinomas. They may also be used in patients in intensive care situations, in patients with acute upper gastrointestinal bleeding, pre- and postoperatively to prevent aspiration of gastric acid and to prevent and treat stress ulceration. Further, they may be useful in the treatment of Helicobacter infections and diseases related to these.

These proton pump inhibitors are, however, susceptible to degradation/transformation in acidic reacting and neutral media The degradation is catalyzed by acidic reacting compounds and the proton pump inhibitors are usually stabilized in mixtures with alkaline reacting compounds.

In respect to the stability properties of the proton pump inhibitors mentioned above, it is obvious that a proton pump inhibitor in an oral solid dosage form must be protected from contact with the acidic reacting gastric juice and the active substance must be transferred in intact form to that part of the gastrointestinal tract where pH is less acidic, neutral or alkaline and where rapid absorption of the pharmaceutically active substance, i.e. the proton pump inhibitor, can occur.

A pharmaceutical dosage form of these proton pump inhibitors is best protected from contact with acidic gastric juice by an enteric coating layer. In U.S. Pat. No. 4,853,230 such enteric coated preparations of different acid labile substances are described. Said preparations contain an alkaline core material comprising the active substance, a separating layer and an enteric coating layer.

Ordinary enteric coating layers, however, comprise compounds which contain acidic groups. If covered with such an enteric coating layer, the acid labile substance may rapidly decompose by direct or indirect contact with the acidic groups resulting in discoloration of the content and loss in content of the active compound with the passage of time. The discoloration can be avoided by applying some type of separating layer between the core material comprising the susceptible proton pump inhibitor and the enteric coating layer.

Thus, there are a lot of patent applications describing such a separating layer between a core material comprising the pharmaceutically active substance and an enteric coating layer. See for instance, U.S. Pat. No. 4,786,505, EP 0,277, 741 and EP 0,342,522. The prior art techniques to apply at least two different layers on a pellet core or a tablet comprising an acid labile compound is rather complicated and there is a demand for finding new processes and formulations to simplify the manufacturing of such enteric coated articles comprising acid labile substances.

SUMMARY OF THE INVENTION

According to one aspect of the invention a new pharmaceutical dosage form is provided in the form of an enteric coated tablet. Alternatively, individually enteric coated units are prepared and filled into a capsule, a sachet or included in a tableted multiple unit dosage form.

The present invention is characterized by the presence of a separating layer between an alkaline reacting core material comprising a pharmaceutically active acid labile substance and an enteric coating layer, wherein the separating layer comprises a water soluble salt of an enteric coating polymer.

According to a second aspect the present invention provides a process for the manufacture of two functionally different layers in one manufacturing step. By such a process a separating layer comprising a water soluble salt of an enteric coating polymer is obtained, as well as the enteric coating layer itself.

Thus, the present invention simplifies the preparation of enteric coated articles comprising a separating layer between a core material and an enteric coating layer by providing a new process for the manufacture of such dosage forms. According to said process the separating layer is formed by an in situ reaction between the enteric coating polymer and the alkaline core material comprising the pharmaceutically active substance.

DETAILED DESCRIPTION OF THE INVENTION

Figure 1:
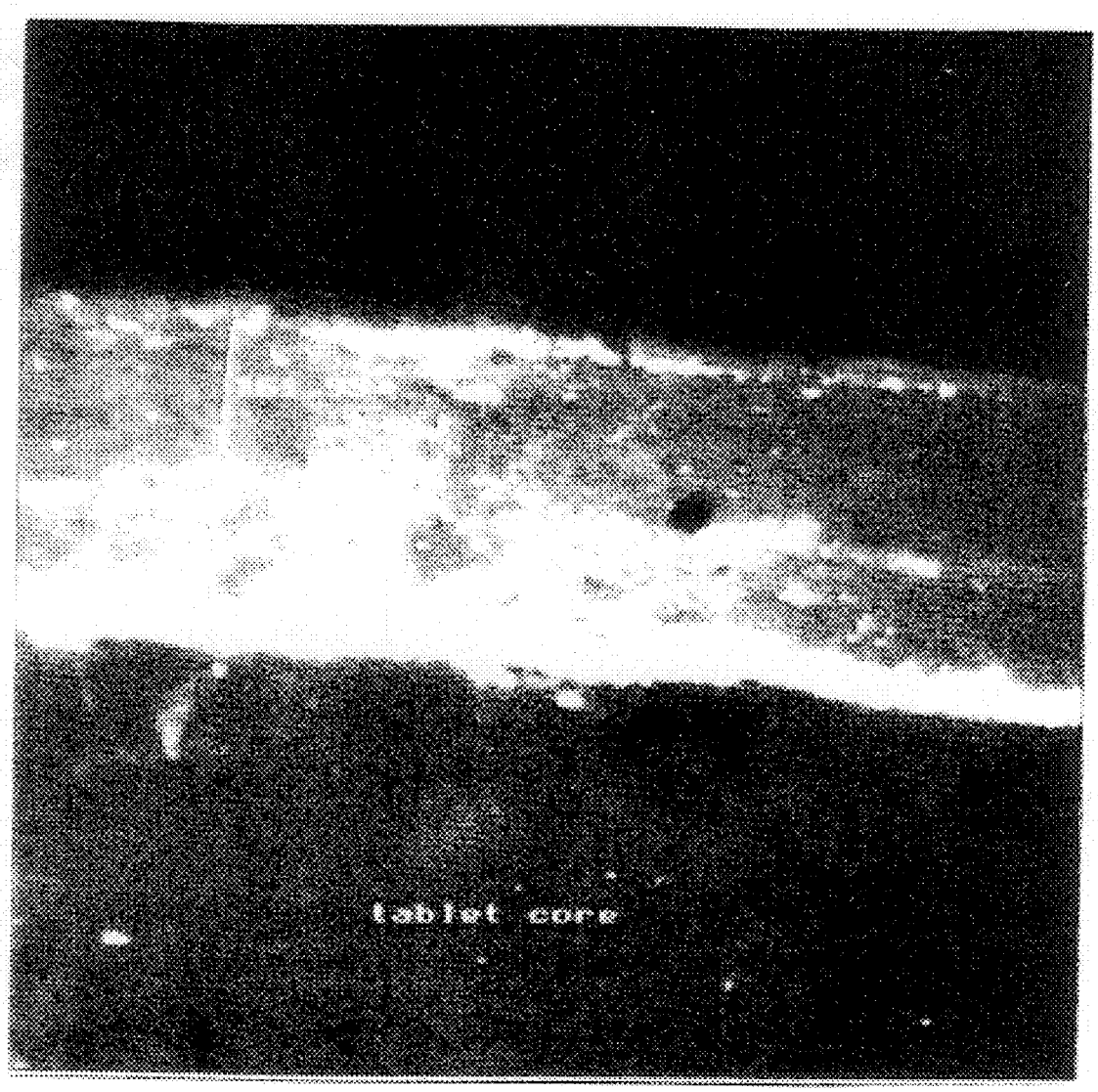
FIG. 1 is a photo showing a cross-section of a tablet manufactured according to the invention described in the present specification.
Figure 2:
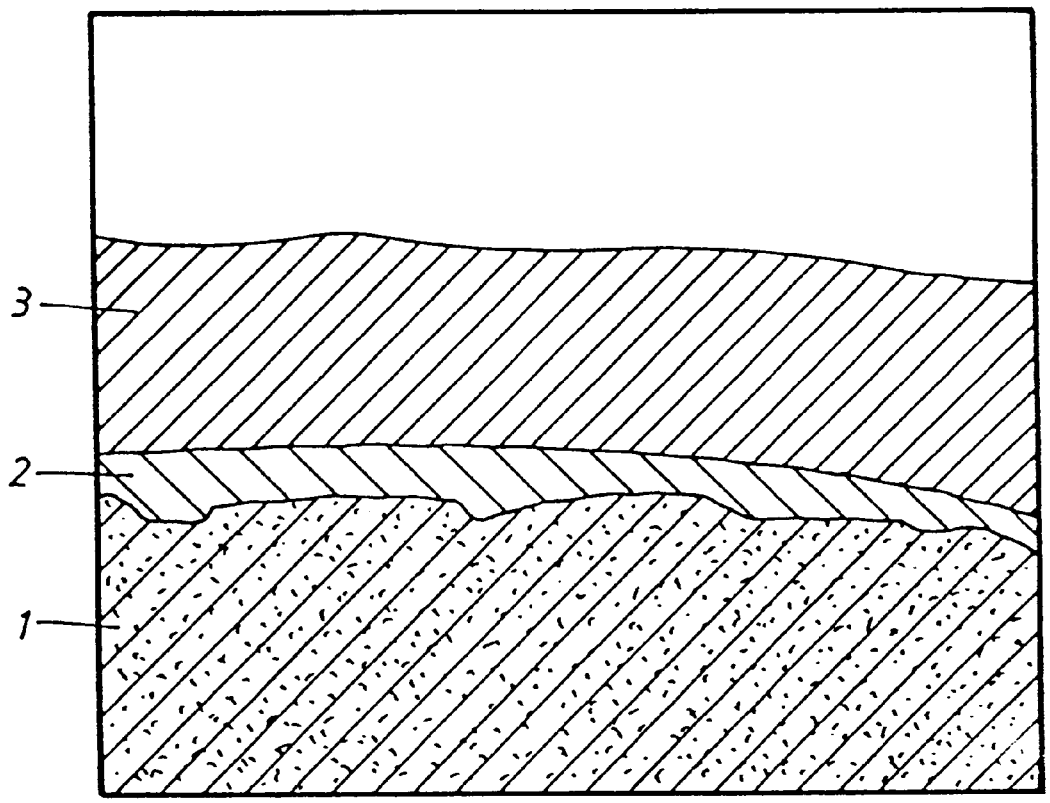
FIG. 2 is a schematic drawing of the photo disclosed in FIG. 1. The tablet has an enteric coating layer (3), which has been applied on an alkaline core material (1) comprising the pharmaceutically active substance. Between the enteric coating layer (3) and the core material (1) there is a separating layer (2) shown. The separating layer (2) is on the photo inked by a fluorescent colour.

One object of the present invention is to provide a new enteric coated pharmaceutical formulation comprising a core material that contains a proton pump inhibitor, one or more alkaline reacting compound(s) and optionally pharmaceutically acceptable excipients, which formulation has a water soluble separating layer and an enteric coating layer and wherein the core material is alkaline and the separating layer is being formed in situ during the enteric coating as a salt between the enteric coating polymer(s) and an alkaline reacting compound(s) in the core material.

Another object of the present invention is to provide a new process for the manufacture of such enteric coated pharmaceutical formulations comprising a core material of a proton pump inhibitor wherein a separating layer is formed in situ during the enteric coating by a reaction between the enteric coating polymer(s) and one or more alkane reacting compound(s) in the core material, i.e. thereby a salt is formed between the enteric coating polymer(s) and the alkaline reacting compound(s).

The new pharmaceutical dosage form according to the invention is further characterized in the following way. Compacted tablets or individual cores (in the form of small tablets, small beads, granules or pellets) contain the proton pump inhibitor in the form of a racemate or one of its single enantiomers or an alkaline salt of said compound or one of its single enantiomers. The tablets or individual cores, that also comprise one or more alkaline reacting compound(s) which is in the position to form a water soluble salt by a reaction with an enteric coating material, are coated with one or more enteric coating layers.

The separating layer is formed in situ by a reaction between the enteric coating polymer(s) and the alkaline reacting compound(s) in the core material during the enteric coating process.

The core material for the manufacture of enteric coated pellets can be prepared according to two main principles. Firstly, seeds can be layered with the proton pump inhibitor, alkaline reating compound(s) and necessary excipients to give an alkaline reacting core material, or the alkaline reacting core material can be prepared as substantially homogeneous cores or is tablets comprising the proton pump inhibitor and the alkaline reacting compound(s).

The alkaline reacting compound(s) in the core material or tablet cores, necessary for an in situ reaction with the enteric coating polymer, is a substance in the position to form a water soluble salt with an enteric coating polymer. Such alkaline reacting compounds are for instance amino acids, such as lysine, arginine, ornitine, histidine, organic buffering compounds such as trometamine (i.e. Tris-buffer), N-amino sugars such as N-methyl-D-glucamine (i.e. Meglumine), N-ethyl-D-glucamine (i.e. Eglumine), glucosamine, disodium-N-stearoyl-glutamate, heterocyclic amine derivatives such as piperazine or its hexahydrate, N-methylpiperazine, morpholine, 1-(2-hydroxyethyl) pyrrolidine, alkali salts of citric acid, tartaric acid, caproic acid or fatty acids, alkali metal phosphates, silicates or carbonates, sodium, potassium, magnesium, calcium or aluminium hydroxides and organic amines such as ethylamine, dicyclohexylamine or triethanolamine, or alkaline ammonium salts.

The core material as such should be an alkaline reacting core material, i.e. the amount of alkaline reacting compound (s) available in the core material should be enough to form a salt between the enteric coating polymer(s) and the alkaline reacting compound(s).

Thus, the concentration of alkaline reacting compound(s) in the core material (before applying the enteric coating polymer) is from approximately 0.1 mmol/g dry ingredients in the alkali containing part of the core material up to approximately 15 mmol/g, preferably the concentration shall be more than 0.3 mmol/g dry ingredients in the alkaline part of the core material.

The upper limit range is only restricted by the need to include a pharmaceutically active ingredient and excipients such as binders etc in the alkaline core material. The concentration of alkaline reacting compound(s) may be illustrated as follows. For a core material where, for instance, 10% w/w of a proton pump inhibitor and 5% w/w of excipients (binders, surfactants etc) are to be included, 85% w/w remains to possible disposition to the alkaline reacting compound(s). For such a core material, this means that, if the alkaline reacting compound is sodium bicarbonate which has the rather low molecular weight of 84%, the concentration of the alkaline material in the core material will be $[(85/84)/100] \times 1000$, i.e. approximately 9.9 mmol/g in the alkali containing part/layer.

One or more enteric coating layers are applied onto the prepared core material or tablets by using a suitable aqueous coating technique. The enteric coating material is dispersed and/or dissolved in an aqueous vehicle. As enteric coating polymer(s) one or more, separately or in combination, of the following can be used; methacrylic acid copolymers, cellulose acetate phthalate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating polymer(s).

The enteric coating layer(s) may contain pharmaceutically acceptable plasticizers to obtain desired mechanical properties, such as flexibility and hardness of the enteric coating layer(s). The amount of plasticizer is optimized for each enteric coating formulation, in relation to selected enteric coating polymer(s), selected plasticizer(s) and the applied amount of said polymer(s). The mechanical properties of the enteric coating are especially important for a tableted multiple unit dosage form, i.e. the individually enteric coated units must withstand the compression into a tableted multiple unit dosage form without any significant effect on the acid resistance. Suitable plasticizers are for instance, but not restricted to, triacetin, citric acid esters, phthalic acid esters, dibutyl sebacate, cetyl alcohol, polyethylene glycols, polysorbates or other plasticizers.

The preparation of the core material containing the proton pump inhibitor and alkaline reacting compound(s) is described more in detail below. The individually enteric coated cores can be constituted according to different principles.

The active substance, the proton pump inhibitor, used as a racemate or one of its single enantiomers or an alkaline salt of said compound or one of its single enantiomers, mixed with the alkaline reacting compound(s) is applied on seeds and are used for further processing.

The seeds, which are to be layered with the active substances, can be water insoluble seeds comprising different oxides, celluloses, organic polymers and other materials, alone or in mixtures or water soluble seeds comprising different inorganic salts, sugars, non-pareils and other materials, alone or in mixtures. Further, the seeds may comprise active substance in the form of crystals, agglomerates, compacts etc. The size of the seeds is not essential for the present invention but may vary between approximately 0.1 and 2 mm. The seeds layered with active substance are produced either by powder or solution/suspension layering using for instance granulating or spray coating/layering equipment.

Before the seeds are layered, the active substance is mixed with alkaline reacting compound(s) and further components to obtain preferred handling and processing properties and suitable concentration of the active substance. Pharmaceutical constituents such as fillers, binders, lubricants, disintegrating agents, surfactants and other pharmaceutically acceptable additives, can be used. Binders are for example celluloses such as hydroxypropyl methylcellulose, hydroxypropyl cellulose and carboxymethylcellulose sodium, polyvinylpyrrolidone, sugars, starches and other pharmaceutically acceptable substances with cohesive properties. Suitable surfactants are formed in the groups of pharmaceutically acceptable non-ionic or ionic surfactants such as a for instance sodium lauryl sulfate or polysorbates.

Alternatively, the active substance mixed with alkaline compound(s) and further mixed with suitable constituents can be formulated into tablets or individual cores. Said tablets or cores may be produced by compression/extrusion/spheronization or balling utilizing different processing equipments. The manufactured tablets or cores can further be layered with additional ingredients comprising active substance and alkaline reacting compound(s) and/or be used for further processing.

The active substance may optionally be mixed with alkaline pharmaceutically acceptable substance (or substances) for further stabilisation. Such substances can be chosen among, but are not restricted to, substances such as for instance the above mentioned alkaline reacting compounds or other alkaline reacting substances known by the skilled person in the art to be useful as stabilizers for acidic susceptable substances.

Alternatively, the aforementioned alkaline reacting core material can be prepared by the use of spray drying or spray congealing technique.

The prepared alkaline reacting core material in the form of tablets or pellets are spray coated with an aqueous enteric coating polymer dispersion/solution. The process parameters such as inlet air temperature, air flow, atomizer air flow and spraying rate are adjusted with respect to the equipment used for the process as well as the specific enteric coating polymer(s). The inlet air temperature must not be such that the enteric coating polymer(s) will block in the spraying nozzles.

The invention is described more in detail by the following examples, which are not intended to limit the scope of the invention.

EXAMPLE 1

Tablets containing lansoprazole and arginine are produced according to the following procedure. Firstly, dry ingredients are thoroughly mixed and then granulated with a solution in a laboratory mixer. The dried granules are mixed with lubricants etc. in a final mixing step.

| Dry ingredients for granulation (for approx. 4000 tablets) | | Concentration (mmol/g dry ingredients in the alkaline tablet core) |
|---|---|---|
| Lansoprazole | 40.4 g | |
| L-arginine (passing 120 mesh) | 365.4 g | 4.2 |
| Microcrystalline cellulose | 38.5 g | |
| Granulating solution | | |
| Distilled water | 173 g | |
| Corn starch | 7.7 g | |

The solution is poured over the premixed powder mass during mixing. The wet granules are dried on a tray in a drying cabinet. The dried granules are milled to pass a 1.0 mm sieve. The granules are mixed with

| Talc | 3.1 g |
|---|---|
| Sodium dodceyl sulphate | 20.8 g |
| Microcrystalline cellulose | 19.2 g |
| Magnesium stearate | 5.0 g | in a laboratory mixer, and then compressed into tablets having a size of 7 mm Ø and a weight of approximately 125 mg. The obtained tablets have a content of lansoprazole of 10 mg per tablet.

Obtained tablets are spray coated with the enteric coating dispersion defined below, in a Wurster equipped fluidized bed.

| Enteric coating dispersion | |
|---|---|
| Water | 80.0 g |
| Triethylcitrate | 1.3 g |
| Na-laurylsulphate | 0.2 g |
| Hydroxypropylmethylcellulose acetate succinate LF | 6.3 g |
| Talc | 1.9 g |

This single coating step resulted in tablets having two polymeric layers with different characteristics. The inner layer is not soluble in acetone, as the outer layer, but soluble in water. FIG. 1, obtained with confocal laser scanning microscopy (CLSM) shows a cross-section of the tablet where the separating layer is easily detected as a layer having an intense fluorescence.

The separating layer is spontaneously formed in situ during the process, as a salt between the alkaline reacting compound and the enteric coating polymer.

EXAMPLE 2

Core material containing the magnesium salt of (−)-omeprazole and the alkaline reacting compound trometamine (=tris-buffer) is prepared by extrusion and spheronization.

The powder mass is mixed in a laboratory mixer and then water is added.

| Powder Mixture | | Concentration (mmol/g dry ingredients in the alkaline core material) |
|---|---|---|
| Magnesium salt of (−)-omeprazole | 400 g | |
| Microcrystalline cellullose | 300 g | |
| Trometamine | 1000 g | 4.1 |
| PVP-XL | 100 g | 4.1 |
| Mannitol pwd | 195 g | |
| Hydroxypropyl methycellullose 6 cps | 5 g | |
| Water | q.s. | |

The powder mixture is mixed with the water and the wet mass is mixed to obtain a suitable consistency of the mass.

Extrusion is performed with an extruder fitted with 1.0 mm screen. The extrudate is formed into pellets on a spheronizer and dried in a fluidized bed drier.

200 g of the obtained pellets are spray coated with the enteric coating dispersion described below, in a Wurster equipped fluidized bed.

| Enteric coating dispersion | |
|---|---|
| Water | 93.9 g |
| Polyethylene glycol 400 | 4.6 g |
| Eudragit ™ L30D-55 | 151.5 g |

This single coating step resulted in pellets having two polymeric layers with different characteristics. The inner layer is not soluble in acetone as the outer layer, but soluble in water. The separating layer is spontaneously formed in situ during the process, as a salt between the alkaline reacting compound and the enteric coating polymer.

Enteric coated pellets having a separating layer are obtained. These pellets may be filled in capsules or sachets for oral administration.

EXAMPLE 3

Core material containing omeprazole and N-methyl-D-glucamine (=-meglumine) is prepared by extrusion and spheronization of the below described composition using the same procedure as in Example 2;

| Powder Mixture | | Concentration (mmol/g dry ingredients in the alkaline core material) |
|---|---|---|
| Omeprazole | 100.0 g | |
| Microcrystalline cellulose | 50.0 g | |
| Meglumine | 500.0 g | 2.6 |
| Mannitol pwd | 297.0 g | |
| Sodium starch glycolate | 48.0 g | |
| Sodium laurylsulphate | 5.0 g | |
| Water | q.s | |

Obtained dried pellets/cores are spray coated with the enteric coating dispersion described below, in a Wurster equipped fluidized bed.

| Enteric coating dispersion | |
|---|---|
| Water | 93.9 g |
| Polyethylene glycol 400 | 4.6 g |
| Eudragit ™ L30D-55 | 151.5 g |

This single coating step resulted in tablets having two polymeric layers with different characteristics. The inner layer is not soluble in acetone, as the outer one, but soluble in water. The separating layer is spontaneously formed in situ during the process, as a salt between the alkaline reacting compound and the enteric coating polymer.

The obtained pellets having a separating layer and an enteric coating layer, are suitable for filling into hard gelatine capsules or sachets for oral administration.

EXAMPLE 4

Core material containing magnesium salt of omeprazole and N-methyl-D-glucamine (meglumine) is prepared by layer coating in a Wurster equipped fluidized bed on sugar seeds. For this operation the following materials are used;

| Substance | Amount | Concentration (mmol/g dry ingredients in the alkali containing layer) |
| --- | --- | --- |
| Water purified | 102 g | |
| Ethanol 99% (w/w) | 102 g | |
| HPMC 6 cps | 2 g | |
| N-methyl-D-glucamine | 3.3 g | 0.37 |
| Magnesium salt of omeprazole | 40 g | |
| Nonpareil | 500 g | |

First the water and ethanol were mixed whereafter the HPMC was dissolved in the obtained solution. N-methyl-D-glucamine and magnesium salt of omeprazole were dissolved/suspended in the solution. The sugar cores (Non Pareille) were used as starting seeds for the formation of core material. A peristaltic pump was used to feed the spraying suspension, which was fed with a velocity of 3.9 g/min.

The Wurster apparatus was equipped with a 60 mm high insertion tube, having a diameter of 50 mm, positioned to leave a 10 mm slit below it. A spraying nozzle having a 0.8 mm opening was used. The atomizing air flow was 2.3 $Nm^3/h$ and air pressure used was 1.9 bar. The inlet air temperature was 50° C. and flow used 43 $m^3/h$.

After the core formation step, 100 grams of the obtained core material was film-coated by spraying with an enteric coating dispersion as described below, using the same equipment as in the core formation step.

| Enteric coating dispersion | |
| --- | --- |
| Water purified | 183 g |
| Triethyl citrate | 2.9 g |
| Sodium laurylsulphate | 0.4 g |
| Hydroxypropyl methylcellulose acetate succinate LF | 14.4 g |
| Talc | 4.3 g |

First the triethyl citrate was dissolved in the water, and thereafter the sodium lauryl sulphate was added. The hydroxypropylmethylcellulose acetate succinate was dispersed in the solution, and then the talc was added. The dispersion was fed with a rate of 3.8 g/min.

Inlet air temperature used was 42° C. and flow was set to 40 $Nm^3/h$. Atomizing air flow used was 2. 1 $Nm^3/h$, obtained with a pressure of 1.7 bar.

After finalizing the spraying, the inlet air temperature was raised to 60° C. and the product was kept at this temperature for appr. 5 minutes.

This single film-coating step resulted in cores having two polymeric coating layers with different characteristics. The inner layer is not soluble in acetone, as the outer layer, but soluble in water. Using confocal laser scanning microscopy to study a cross-section of the cores from this example, the presence of an inner layer was confirmed.

The separating layer is spontaneously formed in situ during the process, as a salt between the alkaline reacting compound and the enteric coating polymer.

EXAMPLE 5

A rotogranulator was used to produce spherical core units containing pantoprazole. As starting material inert sugar seeds (Non-Pareille) with an average size between 0.6 to 0.71 mm Ø was used. The sugar seeds were coating layered with the powder mixture described below, by spraying a 5% solution of HPMC 6 cps in water.

The obtained core material containing pantoprazole was dried at 40° C. for 16 hours in vacuum and then sieved to give granules between 0.6 mm to 1.25 mm Ø.

| Starting material | | |
| --- | --- | --- |
| Non-Pareille | 110 parts by weight | |
| Powder mixture | Amount | Concentration |
| | | (mmol/g dry ingredients in the alkali containing layer) |
| Pantoprazole | 29.3 parts by weight | |
| L-Lysine | 22.0 " | 0.88 |
| Sucrose | 36.7 " | |
| Corn starch | 42.5 " | |
| Microcrystalline cellulose | 36.7 " | |
| Solution | | |
| Hydroxypropyl methylcellulose | 2.9 " | |
| Water | (58.7 ") | |

250 g of the core material produced in this way was spray coated with an enteric coating dispersion in a Wurster equipped fluidized bed apparatus. The dispersion was made by adding the mentioned ingredients in stated order, while stirring.

| Dispersion | |
| --- | --- |
| Water | 626.8 g |
| Triethylcitrate | 9.8 g |
| Sodium-laurylsuphate | 1.5 g |
| Hydroxypropylmethylcellulose acetate succinate LF | 49.2 g |
| Talc | 14.8 g |

Enteric coated pellets having a water soluble separating layer were obtained. These pellets may be filled in capsules or sachets for oral administration.

EXAMPLE 6

Omeprazole tablets, 6 mm in diameter containing 20 mg of omeprazole were prepared by mixing and granulating dry powder ingredients with water in a Kenwood mixer. For this operation the following materials are used;

| Substance | Amount | Concentration (mmol/g dry ingredients in the alkaline tablet core) |
|---|---|---|
| Omeprazole | 40.0 g | |
| Mannitol pwd | 68.0 g | |
| Microcrystalline cellulose | 35.0 g | |
| Polyvinylpyrrolidone cross-linked | 30.0 g | |
| Hydroxypropylcellulose low-substituted | 20.0 g | |
| L-arginine | 5.3 g | 0.14 |
| Sodium laurylsulphate | 2.0 g | |
| Water purified q.s | approx 50 g | |
| Sodium stearylfumarate (SSF) | 1.0 g | |

The dry powders except for SSF were mixed to homogeneity. This mixture was moistened with the water and the wet mass dried on a tray in a drying oven. The obtained granules were milled to pass a screen with 0.8 mm apertures. Then the lubricant SSF was mixed with the granules using the same Kenwood mixer as before.

Cores having an average weight of 101 mg were compressed on a tabletting machine equipped with 6 mm diameter punches.

After the core formation step, 50 grams of the obtained cores were film-coated by spraying an aqueous enteric coating dispersion as described below, using a Wurster equipped fluidized bed.

| Enteric coating dispersion Substance | Amount |
|---|---|
| Water purified | 183 g |
| Triethyl citrate | 2.9 g |
| Sodium laurylsulphate | 0.4 g |
| Hydroxyproplmethylcellulose acetate succinate LF | 14.4 g |
| Talc | 4.3 g |

This single film-coating step resulted in cores having two polymeric coating layers with different characteristics. The inner layer is not soluble in acetone, as the outer layer, but soluble in water.

The separating layer is spontaneously formed in situ during the process, as a salt between the alkaline reacting compound and the enteric coating polymer.

EXAMPLE 7

Tablets, 7 mm in diameter containing omeprazole and disodiumhydrogenphosphate was prepared by mixing and granulating dry powder ingredients with a water solution containing sodium laurylsulphate, in a Kenwood mixer. For this operation the following materials are used:

| Substance | Amount | Concentration (mmol/g dry ingredients in the alkaline tablet core) |
|---|---|---|
| Omeprazole | 80.0 g | |
| Mannitol pwd | 88 g | |
| Microcrystalline cellulose | 132 g | |
| L-HPC | 53 g | |
| Disodiumhydrogenphosphate dihydrate | 104 g | 1.12 |

-continued

| Substance | Amount | Concentration (mmol/g dry ingredients in the alkaline tablet core) |
|---|---|---|
| Granulation liquid | | |
| Water purified | 80 g | |
| Sodium laurylsulphate | 3 g | |
| Water purified q.s | | |
| Final mixing | | |
| Sodium stearylfumarate (SSF) | 10 g | |
| Polyvinylpyrrolidone crosslinked | 50 g | |

The dry powders except for SSF were mixed to homogenity. This mixture was moistened first with the granulation liquid and then with water until satisfactory consistency of the mass. The wet mass was dried on a tray in a drying oven. The obtained granules were milled to pass a screen with 0.8 mm apertures and then the lubricant SSF and the disintegrating agent polyvinylpyrrolidone crosslinked were mixed with the obtained granules using the same Kenwood mixer as before.

Cores having an average weight of 130 mg were compressed on a tabletting machine equipped with 7 mm diameter punches.

After the core formation step, 50 grams of the obtained cores were film-coated by spraying with an aqueous enteric coating dispersion as described below, using a Wurster equipped fluidized bed.

| Enteric coating dispersion | Amount |
|---|---|
| Water purified | 183 g |
| Triethyl citrate | 2.9 g |
| Sodium laurylsulphate | 0.4 g |
| Hydroxypropyl methylcellulose acetate succinate LF | 14.4 g |
| Talc | 4.3 g |

This single film-coating step resulted in cores having two polymeric coating layers with different characteristics. The inner layer is not soluble in acetone, as the outer layer, but soluble in water. The separating layer is spontaneously formed in situ during the process, as a salt between the inorganic alkaline reacting compound and the enteric coating polymer.

REFERENCE EXAMPLES 1 AND 2

Placebo tablets, 6 mm in diameter was prepared by mixing and granulating dry powder ingredients with water in a Kenwood mixer. For this operation the following materials are used;

| | Amount | | Concentration (mmol/g dry ingredients in the alkali containing layer) | |
|---|---|---|---|---|
| Substance | Ref. Ex. 1 | Ref. Ex. 2 | Ref. Ex. 1 | Ref. Ex. 2 |
| Mannitol pwd | 161.5 g | 141.3 g | | |
| Microcrystalline cellulose | 38.5 | 38.5 | g | g |

15

-continued

| | Amount | | Concentration (mmol/g dry ingredients in the alkali containing layer) | |
|---|---|---|---|---|
| | Ref. | Ref. | Ref. | Ref. |
| Substance | Ex. 1 | Ex. 2 | Ex. 1 | Ex. 2 |
| $Na_2HPO_4 \times 2H_2O$ | — | 20.2 g | — | 0.56 |
| Water purified q.s. | approx. 45 g | 45 g | | |
| Sodium stearylfumarate (SSF) | 1.0 g | 1.0 g | | |

The dry powders except for SSF were mixed to homogeneity. This mixture was moistened with the water and the wet mass dried on a tray in a drying oven. The obtained granules were milled to pass a screen with 0.8 mm apertures. Then the lubricant SSF was mixed with the granules using the same Kenwood mixer as before.

Cores having an average weight of 93–94 mg were compressed on a tableting machine equipped with 6 mm diameter punches.

After the core formation step, 50 grams of each kind of the obtained cores were (separately) film-coated by spraying an aqueous enteric coating dispersion according to below, using a Wurster equipped fluidized bed.

| Enteric coating dispersion Substance | Amount |
|---|---|
| Water purified | 183 g |
| Triethyl citrate | 2.9 g |
| Sodium laurylsulphate | 0.4 g |
| Hydroxypropylmethycellulose acetate succinate LF | 14.4 g |
| Talc | 4.3 g |

These reference examples show that presence of the alkaline material in the core material composition is necessary for the formation of an in situ formed spontaneously developed separating layer.

For Reference Ex. 1, this single film-coating step resulted in cores having only one coating layer, being soluble in acetone. No separating layer was spontaneously formed.

For Reference Ex. 2, this single film-coating step resulted in cores having two polymeric coating layers with different characteristics. The inner layer is not soluble in acetone, as the outer layer, but soluble in water. The separating layer is spontaneously formed in situ during the process, as a salt between the alkaline reacting compound and the enteric coating polymer.

By using confocal laser scanning microscopy to study a cross-section of the cores from the Reference example 2, the presence of an inner layer was confirmed. In contrast, examining a cross-section of a core from Reference example 1, no inner layer was seen.

The best mode to practice the invention is by the formulations described in Examples 1 and 2.

The different active substances, i.e. proton pump inhibitors, are prepared according to information disclosed in the Patent specifications mentioned in page 6 of this specification.

What is claimed is:

1. A process for preparing an oral pharmaceutical formulation comprising the steps of:

16 forming a core material comprising a proton pump inhibitor and at least one alkaline reacting compound, wherein the concentration of the alkaline reacting compound is about 0.1 mmol/g dry ingredients in the alkaline containing part of the core material, and applying an enteric coating polymer layer so as to surround the core material thereby forming in situ a separating layer as a water soluble salt product between the alkaline compound and the enteric coating polymer.

2. The process according to claim 1, wherein the proton pump inhibitor is a compound of the general formula I or a pharmaceutically acceptable salt thereof or a pure enantiomer thereof in neutral form or in the form of an alkaline salt,

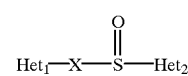

I wherein $Het_1$ is

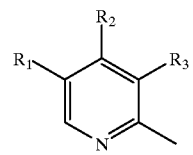

or

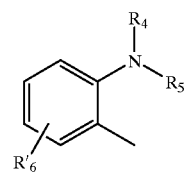

wherein $Het_2$ is

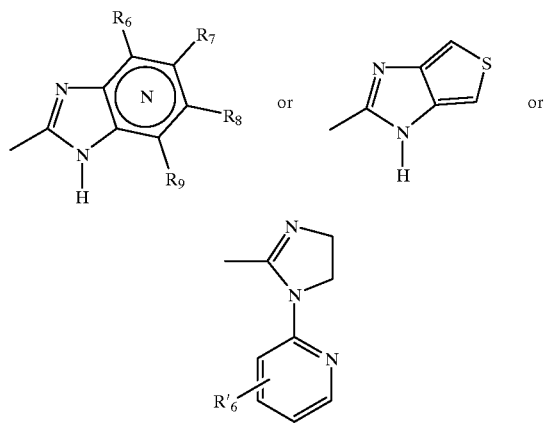

X=

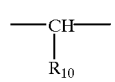 or 

wherein N in the benzimidazole moiety means that one of the carbon atoms substituted by $R_6$–$R_9$ may be exchanged for a nitrogen atom without any substituents;

$R_1$, $R_2$ and $R_3$ are the same or different and selected form the group consisting of hydrogen, alkyl, and alkoxy, unsubstituted or substituted by fluorine, alkylthio, alkoxyalkoxy, dialkylamino, piperidino, morpholino, halogen, phenyl and phenylalkoxy;

$R_4$ and $R_5$ are the same or different and selected from the group consisting of hydrogen, alkyl and aralkyl;

$R_6$ is hydrogen, halogen trifluoromethyl, alkyl or alkoxy;

$R_6$–$R_9$ are the same or different and selected from the group consisting of hydrogen, alkyl, alkoxy, halogen, halo-alkoxy, alkylcarbonyl, alkoxycarbonyl, oxazolyl, and trifluoroalkyl; or adjacent groups $R_6$–$R_9$ form ring structures which may be further substituted;

$R_{10}$ is hydrogen or forms an alkylene chain together with $R_3$ and $R_{11}$ and $R_{12}$ are the same or different and selected from the group consisting of hydrogen, halogen alkyl, and alkoxy, which alkyl or alkoxy may be branched or a straight $C_1$–$C_9$-chain or a cyclic alkyl.

3. The process according to claim 1, wherein the proton pump inhibitor is omeprazole, an alkaline salt of omeprazole, a pure enantiomer of omeprazole or an alkaline salt of the enantiomer.

4. The process according to claim 1, wherein the proton pump inhibitor is lansoprazole, a pharmaceutically acceptable salt of lansoprazole, a pure enantiomer of lansoprazole or a pharmaceutically acceptable salt of the enantiomer.

5. The process according to claim 1, wherein the proton pump inhibitor is pantoprazole, a pharmaceutically acceptable salt of pantoprazole, a pure enantiomer of pantoprazole or a pharmaceutically acceptable salt of the enantiomer.

6. The process according to claim 1, wherein the core material is in the form of a tablet.

7. The process according to claim 1, wherein the alkaline reacting compound is selected from the group consisting of an alkaline reacting organic compound, a hydroxide of an alkali metal, an alkaline salt of phosphoric acid, carbonic acid or silicic acid, and an alkaline ammonium salt.

8. The process according to claim 1, wherein the alkaline reacting compound is a hydroxide of an alkali metal.

9. The process according to claim 1, wherein the alkaline reacting compound is an alkaline salt of phosphoric acid, carbonic acid or silicic acid.

10. The process according to claim 1, wherein the alkaline reacting compound is an alkaline ammonium salt.

11. The process according to claim 1, wherein the alkaline reacting compound is an alkaline reacting organic compound is an amino acid or a salt of the amino acid.

12. The process according to claim 11, wherein the amino acid is selected from the group consisting of lysine, arginine, ornitine and histidine.

13. The process according to claim 1, wherein the alkaline reacting compound is an alkaline reacting compound selected from the group consisting of an alkaline amine, a derivative of the alkaline amine and an alkaline salt of a weak organic acid.

14. The process according to claim 13, wherein the derivative of the alkaline amine is N-methyl-D-glucamine or tromethamine.

15. The process according to claim 1, wherein the enteric coating polymer is dispersed and/or dissolved in an aqueous vehicle.

16. The process according to claim 1, wherein the enteric coating polymer a hydroxypropyl cellulose derivative.

17. The process according to claim 16, wherein the hydroxypropyl cellulose derivative is a hydroxypropylmethyl cellulose acetate succinate.

18. The process according to claim 1, wherein the enteric coating polymer is a copolymer of methacrylic acid or methylmethacrylate ester.

19. The process according to claim 2, wherein the cyclic alkyl group is a cycloalkyl-alkyl.

20. The process according to claim 1, wherein the core material further comprises a pharmaceutically acceptable excipient.

21. The process according to claim 1, wherein the core material is in the form of a pellet or a plurality thereof.

* * * * *

UNITED STATES PATENT AND TRADEMARK OFFICE
CERTIFICATE OF CORRECTION

PATENT NO. : 6,013,281

DATED : January 11, 2000

INVENTOR(S) : Lundberg et al.

It is certified that error appears in the above-identified patent and that said Letters Patent is hereby corrected as shown below:

Claim 1, col. 16, line 4, delete "about" and insert therefor -- more than --, and at line 9, after "alkaline", insert -- reacting --.

Claim 2, col. 17, line 11, delete "$R_6$" and insert therefor --$R'_6$--.

Signed and Sealed this

Seventh Day of November, 2000

Attest:

Q. TODD DICKINSON

*Attesting Officer*    *Director of Patents and Trademarks*